United States Patent [19]

Rankin

[11] 4,127,423

[45] Nov. 28, 1978

[54] CONTACT LENS CLEANING SOLUTION

[75] Inventor: Billy F. Rankin, Rockville, Md.

[73] Assignee: Burton, Parsons and Company, Inc., Washington, D.C.

[21] Appl. No.: 832,885

[22] Filed: Sep. 13, 1977

[51] Int. Cl.$^2$ .................. B08B 3/10; B08B 11/00; C11D 7/10

[52] U.S. Cl. .................. 134/30; 252/89 R; 252/106; 252/DIG. 5; 252/DIG. 8; 252/DIG. 14; 424/127; 424/153; 424/184; 134/26; 134/42

[58] Field of Search .................. 252/135, 89, 99, 106, 252/173, DIG. 5, DIG. 8, DIG. 14; 424/127, 153, 184; 134/30, 26, 42

[56] References Cited

U.S. PATENT DOCUMENTS

| | | | |
|---|---|---|---|
| 3,240,209 | 3/1966 | Rankin | 252/106 |
| 3,847,663 | 11/1974 | Shumaker | 252/135 L |
| 3,908,680 | 9/1975 | Krezanoski | 134/27 |

OTHER PUBLICATIONS

"PQ Soluble Silicates for Detergent Formulations" Philia. Quartz Co., 1960, p. 5.
"Inorganic Components of Detergents Table XIII, p. 51, in Synthetic Detergents, Davidsohn et al., 1967.

*Primary Examiner*—Mayer Weinblatt
*Attorney, Agent, or Firm*—Fidelman, Wolffe & Waldron

[57] ABSTRACT

Silicone and/or hydrophilic soft contact lenses are freed of proteinaceous and other deposits by rubbing them with an aqueous solution of a crystalline sodium silicate having a pH of 10.2 - 10.9 and rinsing. The solution may contain in addition sodium chloride in isotonic amount, viscosity agents, wetting agents, detergents and bactericides.

13 Claims, No Drawings

CONTACT LENS CLEANING SOLUTION

This application is related to Ser. No. 751,068, filed Dec. 16, 1976, now U.S. Pat. No. 4,065,324.

The present invention relates to a cleansing composition for contact lenses and similar opthalmic apparatuses, particularly to a cleansing composition which may be utilized to remove heavy proteinaceous and other encrustations from both silicone and hydrophilic contact lenses and more particularly to a cleansing composition which comprises a sodium silicate solution to be utilized to clean soft contact lenses.

Soft contact lenses may be divided into two broad categories, namely hydrophilic and hydrophobic lenses. Hydrophobic contact lenses are usually based on elastic and flexible silicone rubber (polysiloxane), and are generally made from cross-linked dimethyl polysiloxane. A typical preparation of a silicone contact lens is disclosed in U.S. Pat. No. 3,228,741, which is hereby incorporated by reference and comprises forming a mixture of a suitable polymerization catalyst, up to 40% of a silica filler, and the silocone polymer. Said mixture is then molded and cured by heating to cross-link the polysiloxane and to produce a finished clear lens. Increased consumer acceptance of flexible silicone rubber lenses has created a need for a cleaning solution which can be used effectively with such lenses.

Hydrophilic soft contact leanses are hydrated gel lenses which can be prepared by copolymerizing hydrophilic organic monomers containing an olefinic double bond with a small amount of a cross-linking agent which usually contains two polymerizable olefinic double bonds. These lenses are usually based on polyhydroxylated alkyl methacrylates and contain a polyhydroxylated alkyl methacrylate, such a polyhydroxyethyl methacrylate, cross-linked with, for example, an hydroxyethyl dimethacrylate.

Hydrated gel lenses can contain the following materials: (1) hydroxyethylmethacrylate or its analogs, (2) ethyleneglycol dimethacrylate or its analogs, (3) polymethylmethacrylate or its analogs, (4) polyvinylpyrrolidone, (5) traces of the respective monomers, (6) traces of inhibitors such as hydroquinone, (7) traces of catalysts such as benzoyl peroxide, and (8) water.

Many different cold detergent solutions have been formulated for cleaning contact lenses. The continued and repeated use of some of these solutions has the effect of keeping dirt from accumulating on the lenses. However, these compositions have limited efficacy on neglected, severely encrusted lenses. Hydrophilic gel lenses are particularly susceptible to severe encrustations of protein and other tear deposits because such lenses are often subjected to heat treatment, such as boiling in saline, to sterilize the lenses. The heat treatment of hydrophilic gel lenses that have not been adequately cleaned prior to heat treatment can denature any tear proteins remaining on the lenses and make subsequent removal of the proteins more difficult.

U.S. Pat. No. 3,908,680 discloses a method for cleaning heavily encrusted contact lenses by successively immersing them in two aqueous solutions. Each solution contains an active oxygen-yielding peroxy compound and preferably a chelating agent. One of the solutions is made acidic and the other basic. Although this method is reasonably effective, it suffers from the disadvantage of inconvenience because of the necessity of employing two different solutions. In effect the lenses must be cleaned twice.

U.S. Pat. No. 3,829,329 discloses the toughening of the surface and cleaning of a soft hydrophilic contact lens with hydrogen peroxide solution.

U.S. Pat. No. 3,240,709 discloses the cleansing of contact lenses with a buffered methylcellulose solution which is effective for removing crystalline tear deposits from the lenses. Presumably the contact lens is a hard lens.

A need exists therefore for a contact lens cleaning solution which can remove deposits from both hydrophilic and silicone lenses and can do so more readily than existing methods. The primary object of this invention is to provide such a cleaning composition.

In accordance with the present invention aqueous solutions of sodium silicates are utilized to quickly and easily clean proteinaceous and other encrustations from hydrophilic or silicone contact lenses.

Sodium silicate has found use in the prior art as a cleaning agent for various materials. U.S. Pat. Nos. 3,847,663 and 3,870,560 disclose the use of alkali metal silicates in the cleaning of metals.

U.S. Pat. No. 3,915,738 discloses the use of a water soluble alkali metal silicate in the preparation of a catalyst used in preparing an aqueous composition for cleaning glass windows and mirrors.

U.S. Pat. No. 3,491,029 discloses a bottle cleansing agent which is partially composed of sodium silicate.

The use of a sodium silicate solution of clean contact lenses is unprecedented and the ability with which it removes proteinaceous and other tear deposits therefrom is entirely unexpected in view of the prior art.

Soluble silicates are composed of varying proportions of sodium oxide, silica and water. Depending on their composition, they provide a wide range of chemical and physical properties. Sodium silicates are manufactured by combining alkali and a specially selected silica at high temperatures. The resulting product is a glass which can be dissolved by special processes to produce the various silicate solutions.

Theoretically, silica and alkali can be combined in all proportions above 1:1, but present products do not exceed a silica to alkali ratio of about four to one by weight because of the very low solubility of fused silicates above this ratio. The compositions of crystalline silicates that are definite chemical compounds can be identified by specific formulas. For example, anhydrous metasilicate is designated as $Na_2SiO_3$. Most silicates, however, are glassy combinations of alkali and silica, best identified by the ratio of components, e.g., a silicate with a weight ratio of 3.22 parts silica and 1 part alkali: $SiO_2/Na_2O$ of 3.22.

Since a molecule of $Na_2O$ weighs very nearly the same as a molecule of $SiO_2$, the molecular ratio and weight ratio are very nearly equal. Consequently, it has become standard practice to use weight ratios for sodium silicates more siliceous than the metasilicate (1:1). The silicates of alkalinity greater than $SiO_2/Na_2O = 1.60$ are not glasses but are definite crystalline compounds of fixed composition. Sodium metasilicate, sodium sesquesilicate and sodium orthosilicate are examples of such silicates.

All sodium silicates are alkaline in reaction. The buffer capacity, i.e., the ability of the solution to resist changes in pH, increases with increasing proportions of soluble silica. Dilute silicate solutions will maintain a fairly constant pH despite the addition of acid.

According to the present invention a dilute solution of a crystalline sodium silicate is formulated in water, and the pH is adjusted to approximately 10.2 to 10.9 to form a contact lens cleaning solution.

Suitable crystalline sodium silicates include sodium orthosilicate, sodium metasilicate and sodium sesquisilicate, such as those marketed by the Philadelphia Quartz Co., Valley Forge, Pa.

The soluble silicate is preferably incorporated into the solution to the extent of 0.1 to 5 percent by weight, most preferably 0.5 to 1 percent by weight.

Any adjustments to the pH of the silicate solutions are made by the addition of dilute hydrochloric acid thereto until the 10.2–10.9 pH is achieved. Buffering of the solution is unnecessary, a further advantage over prior art cleaning solutions.

Since the silicate ion is precipitated from solution by salts of various metals, such as calcium, magnesium, aluminum, titanium, copper and lead, the water used to prepare the cleaning solution of the present invention should be dionized or distilled.

Contact lenses may be cleaned with the solution of the present invention by applying a few drops of said solution to the lens, rubbing the lens between the thumb and forefinger and rinsing the lens with water. For removing heavier encrustations the lenses may be heated in the cleaning solution and rinsed with water. The quantity of solution employed should be sufficient to completely cover the lenses and is thus dependent on the size and shape of the container employed. Therefore, any convenient volume is suitable, although 5 to 25 ml is usually sufficient per pair is lenses to avoid wasting the solution. The solution containing the immersed lenses is heated to a temperature of from 40° to 100° C. for 1 to 5 minutes. Heating to boiling is preferable by virtue of its convenience.

The sodium silicate cleansing solution may consist of essentially sodium silicate dissolved in water, with the pH adjusted by means of dilute HCl, or it may comprise in addition other ingredients to enhance its cleansing power and improve the stability. A typical isotonic formulation is the following present in by weight:

|  | Broad Range | Preferred |
|---|---|---|
| Sodium Chloride | .458 | .458 |
| EDTA | .05 – 0.3 | 0.1 |
| Hydroxyethylcellulose | 0.4 – 0.9 | 0.8 |
| Gelvatol 40/20[1] | 0.5 – 0.9 | 0.75 |
| Sodium Silicate[2] | 0.2 – 1.5 | 0.5 |
| Tyloxapol[3] | 0.1 – 0.4 | 0.2 |
| Thimerosal[4] | .002 – .005 | .004 |
| Distilled or deionized water | balance | balance |
| Dilute HCl added to adjust pH to 10.2 – 10.9 | | |

[1]Polvinylalcohol, product of Shawinigan Products Corp.
[2]Metso 20, a pentahydrate sodium metasilicate product of Philadelphia Quartz Co.
[3]Oxyethylated tertiary octylphenol formaldehyde polymer
[4]Sodium ethylmercurithiosalicylate The sodium chloride is employed in the amount required for an isotonic solution. The EDTA serves as a stabilizer and has bactericidal properties. Hydroxyethyl cellulose serves as a viscosity control agent, Gelvatol 40/20 as a wetting agent, tyloxapol as a detergent, thimerosal as a bactericide and the sodium silicate as the protein removing agent.

Other materials may be substituted for those shown. Thus, the hydroxyethylcellulose may be replaced by other cellulose derivatives such as methylcellulose, hydroxypropylcellulose, carboxymethylcellulose or hydroxypropylmethylcellulose. Other non-ionic detergents which may be substituted for tyloxapol, include Pluronics F68 and F131 which are ethylene oxide-propylene oxide-propylene glycol condensation products (sold by Wyandotte Chemical Corp.) and Tweens (polyalkylene oxide derivatives of sorbitan mono esters of higher fatty acids) having an HCB factor of 12 or over (sold by Atlas Powder Co.) Other bactericides such as chlorhexidine may be substituted for the thimerosal.

For a clearer understanding of the invention, specific examples are set forth below. These examples are merely illustrative and are not to be understood as limiting the scope and underlying principles of the invention in any way. All percentages are by weight.

EXAMPLE 1

A 0.5% solution of sodium sesquisilicate (Metso 99, Philadelphia Quartz Company, Valley Forge, Pa.) is prepared in deionized water, and the pH of the solution is adjusted to approximately 10.5 with dilute hydrochloric acid.

Silicone contact lenses heavily encrusted with deposits are placed in 5 ml of the above solution and heated to boiling for three minutes. The lenses are removed from the solution and rinsed thoroughly with deionized water to completely free them of deposits.

EXAMPLE 2

Silicone lenses less heavily encrusted than those of Example 1 are cleaned by digital manipulation with a few drops of the solution of Example 1 and rinsed with deionized water to completely free them of deposits.

EXAMPLE 3

Example 2 is repeated with additional silicone lenses excrusted with deposits. After digital manipulation and rinsing with deionized water, some deposits may remain on the lenses. The partially cleaned lenses are then subjected to the heat treatment of Example 1 and rinsed to completely remove the deposits.

EXAMPLE 4

Examples 1 to 3 are repeated with encrusted hydrophilic lenses with the same results.

EXAMPLE 5

Examples 1–4 are repeated with an aqueous solution of sodium metasilicate with the same results as with sodium sesquisilicate solution.

EXAMPLE 6

Examples 1–4 are repeated with an aqueous solution of sodium orthosilicate with the same results as with sodium sesquisilicate solution.

EXAMPLE 7

Examples 1–4 were repeated with an isotonic sodium silicate solution having the following composition:

| Ingredient | % by Weight |
|---|---|
| Sodium Chloride | .458 |
| EDTA | 0.1 |
| Hydroxyethylcellulose | 0.8 |
| Gelvatol 40/20 | 0.75 |
| Sodium Silicate | 0.5 |
| Tyloxapol | 0.2 |
| Thimerosal | .004 |
| Distilled or deionized water | balance to 100% |
| Dilute HCl was added to adjust the pH to about 10.5 | |

Upon examination, the lenses were found free of deposits.

While the particular compositions and process herein described are well adapted to carry out the objects of the present invention, it is to be understood that various modifications and changes may be made and this invention is of the scope set forth in the appended claims.

What is claimed:

1. A composition for cleaning hydrophobic silicone or hydrophilic soft contact lenses, comprising a solution in deionized distilled water of 0.2–1.5% of a sodium silicate having a $SiO_2:Na_2O$ ratio of 1:1 to 4:1, an isotonic amount of sodium chloride, about 0.5 to 0.3 of ethylenediamine tetraacetic acid, about 0.4–0.9% a cellulose derivative viscosity control agent, about 0.5–0.9% of polyvinylalcohol, about 0.1–0.4% of a nonionic detergent about .002–.005% of a bactericide, and the balance deionized or distilled water, all percentage being by weight, and sufficient dilute HCl to achieve a pH of about 10.2 to 10.9.

2. The composition of claim 1 wherein the sodium chloride is present in the amount of about 0.458%, the cellulose derivative is selected from the group consisting of hydroxyethylcellulose, methylcellulose, hydroxypropylcellulose, carboxymethylcellulose and hydroxypropylmethylcellulose, the non-ionic detergent is selected from the group consisting of tyloxapol, ethylene oxide - propylene oxide - propylene glycol condensation products and polyalkylene oxide derivatives of sorbitan mono esters of higher fatty acids having an HCB factor of 12 or more and the bactericide is selected from the group consisting of thimersol and chlorhexidine.

3. The composition of claim 2 consisting essentially in percent by weight,

| | |
|---|---|
| Sodium Chloride | .458 |
| [EDTA] Ethylenediaminetetraacetic acid | 0.1 |
| Hydroxyethylcellulose | 0.8 |
| Polyvinylalcohol | 0.75 |
| Sodium Silicate | 0.5 |
| tyloxapol | 0.2 |
| thimersol | .004 |
| Distilled or Deionized Water | balance to 100% |
| Dilute HCl to bring the pH to about 10.2 to 10.9 | |

4. A method of cleaning proteinaceous and other tear deposits from hydrophilic or hydrophobic soft contact lenses which comprises applying to said lenses a few drops of an aqueous solution containing about 0.2–1.5% of a cystalline sodium silicate, said solution having a pH of about 10.2–10.9, rubbing the lenses with the fingers and rinsing with water.

5. A method of cleaning proteinaceous and other tear deposits from hydrophilic or hydrophobic soft contact lenses which method comprises heating said lenses in an aqueous solution having a pH of about 10.2 to 10.9 and containing about 0.2 to 1.5% by weight of a crystalline sodium silicate, removing the lenses and rinsing the lenses with deionized or distilled water.

6. The method of claim 5 wherein the solution containing the lenses is heated to a temperature of from about 40° to 100° C.

7. The method of claim 6 wherein the solution containing the lenses is heated for 1 to 5 minutes.

8. The method of claim 4 wherein the aqueous solution is that of claim 2.

9. The method of claim 4 wherein the aqueous solution is that of claim 3.

10. The method of claim 5 wherein the aqueous solution is that of claim 2.

11. The method of claim 5 wherein the aqueous solution is that of claim 3.

12. The method of claim 11 wherein the solution containing the lenses is heated to a temperature of from about 40° to 100° C.

13. The method of claim 12 wherein the solution containing the lenses is heated for 1 to 5 minutes.

* * * * *